United States Patent
Lecat (10) Patent No.: US 8,323,031 B2
(45) Date of Patent: Dec. 4, 2012

(54) AUSCULTATION TRAINING SYSTEM AND RELATED METHODS

(76) Inventor: Paul Jacques Charles Lecat, Tallmadge, OH (US)

(*) Notice: Subject to any disclaimer, the term of this patent is extended or adjusted under 35 U.S.C. 154(b) by 253 days.

(21) Appl. No.: 12/776,352

(22) Filed: May 7, 2010

(65) Prior Publication Data
US 2010/0279262 A1 Nov. 4, 2010

Related U.S. Application Data

(63) Continuation-in-part of application No. 11/935,468, filed on Nov. 6, 2007, and a continuation-in-part of application No. 12/206,131, filed on Sep. 8, 2008.

(51) Int. Cl.
*G09B 11/00* (2006.01)
(52) U.S. Cl. .......................... 434/268; 434/266
(58) Field of Classification Search .................. 434/262, 434/266, 268
See application file for complete search history.

(56) References Cited

U.S. PATENT DOCUMENTS

| | | | |
|---|---|---|---|
| 3,665,087 A | 5/1972 | Poylo | |
| 3,947,974 A | 4/1976 | Gordon et al. | |
| 4,770,189 A | 9/1988 | Shyu | |
| 6,220,866 B1 | 4/2001 | Amend et al. | |
| 6,461,165 B1 | 10/2002 | Takashina et al. | |
| 6,503,087 B1 | 1/2003 | Eggert et al. | |
| 6,527,559 B2 | 3/2003 | Yoshii et al. | |
| 6,758,676 B2 | 7/2004 | Eggert et al. | |
| 7,115,102 B2 | 10/2006 | Abbruscato | |
| 7,209,796 B2 | 4/2007 | McKinney et al. | |
| 7,289,634 B2 | 10/2007 | Grove | |
| 2003/0002685 A1 | 1/2003 | Werblud | |
| 2004/0076303 A1 | 4/2004 | Vyshedsky et al. | |
| 2004/0157612 A1 | 8/2004 | Kim | |
| 2005/0048455 A1 | 3/2005 | Hayamizu et al. | |
| 2005/0131307 A1 | 6/2005 | Ruiter et al. | |
| 2005/0148283 A1 | 7/2005 | Schwalm | |
| 2005/0181342 A1 | 8/2005 | Toly | |
| 2006/0129067 A1 | 6/2006 | Grajales et al. | |
| 2007/0117077 A1 | 5/2007 | Gordon et al. | |
| 2007/0178430 A1 | 8/2007 | Lecat | |

FOREIGN PATENT DOCUMENTS

| | | |
|---|---|---|
| JP | 09-146452 | 6/1997 |
| JP | 2005-077521 | 3/2005 |
| JP | 2005-227534 | 8/2005 |
| KR | 10-2006-0025301 A | 3/2006 |
| WO | 2006047400 A2 | 5/2006 |

OTHER PUBLICATIONS

Technology to Inspire: Technology Archive Electronic Stethoscope, web page article, Feb. 2007, http://www.youngforesight.org/default.asp?section=Technology&chapter=CAT003.
International Preliminiary Report on Patentability, dated Mar. 15, 2011, World Intelluctual Property Organization, PCT/US2008/082417.
Supplementary European Search Report and Written Opinion, dated Jan. 27, 2011, European Patent Office, EP08847944.9.
International Search Report, dated Jul. 14, 2009, Korean Intellectual Property Office, PCT/US2008/082417.

*Primary Examiner* — Kathleen Mosser
(74) *Attorney, Agent, or Firm* — Roger Emerson; Emerson, Thomson Bennett (57) ABSTRACT

An auscultation training device that utilizes a medical training mannequin, a controller, and a database of auscultation training sound data to simulate and communicate the sounds of the human body to users; the invention is able to initiate the playback of prerecorded sounds via a variety of trigger mechanisms, and transmit live sounds, or combinations of sounds, to remote examiners.

20 Claims, 9 Drawing Sheets

AUSCULTATION TRAINING SYSTEM AND RELATED METHODS

This application is a continuation-in-part of, and claims priority to, U.S. patent application Ser. No. 11/935,468 filed on Nov. 6, 2007 and now pending, and U.S. patent application Ser. No. 12/206,131 filed on Sep. 8, 2008 now pending, both of which are incorporated herein by reference in their entirety.

I. BACKGROUND OF THE INVENTION

A. Field of Invention

Embodiments are directed to devices, methods, and systems relating to auscultation training.

B. Description of the Related Art

Auscultation is the act of listening to sounds within the body as a method of diagnosis. A stethoscope is an example of an auscultation device that is used in the medical field to listen to internal sounds in the human body, such as for example heart sounds, breathing (breath sounds), intestinal noises, and blood flow in arteries and veins. Acoustic stethoscopes operate on the transmission of sound from a headpiece, via air-filled hollow tubes, to a listener's ears. The headpiece may include a diaphragm that can be placed against a human body for sensing sound. Body sounds vibrate the diaphragm, creating acoustic pressure waves that travel through the tubing to the listener's ears.

One common medical examination method, referred to as percussion examination (which includes variants such as routine auscultatory percussion, coin percussion, or sound transmission through bone), comprises propagating an acoustic wave through a part of the body using mild tap-like impacts, such as may be produced by the fingers, and listening to the sound produced in the body. An acoustic wave produced in this way changes resonance according to the size and density of internal structures. This type of examination is often used, for instance, in examining the chest or back.

Using a stethoscope or other auscultation device to diagnose a patient requires training in detecting and identifying abnormal sounds. Standardized patients are a valuable training tool in medical education and have been extensively researched. Though standardized patients give students one-on-one interaction with real human subjects, most standardized patients do not present abnormal symptoms. As a result, simulators and mannequins are often used to train or test students on auscultation devices, such as stethoscopes. Auscultation training mannequins may include a sound generating device embedded within the body of the mannequin to produce sounds consistent with an abnormal physical condition, which students must detect and identify.

Unfortunately, the state of the art still has many shortcomings. Some embodiments differ from the current state of the art, and may provide one or more improvements.

II. SUMMARY OF THE INVENTION

Some embodiments relate to an auscultation training device, comprising: a medical training mannequin which may include means for detecting the position of an auscultation device relative to the mannequin; a controller which may be in electronic communication with the means for detecting relative position and the controller is adapted to receive location data from the means for detecting relative position, wherein the data indicates the position of the auscultation training device relative to the medical training mannequin; a database of auscultation training sound data in electronic communication with the controller, wherein the controller is adapted to select and retrieve auscultation sound data corresponding to data received from the means for detecting relative position; a sound generating device in electronic data communication with the database and adapted to convert sound files communicated therefrom into acoustic wave signals; and an auscultation device having at least one ear piece in acoustic communication with the sound generating device and adapted to transmit acoustic wave signals to a human ear.

Other embodiments relate to a process for auscultation training, comprising the steps of: simulating a patient; detecting the position of an auscultation device relative to the simulated patient; selecting one or more a auscultation sound data files from a database, wherein the selected sound corresponds to the detected relative position of the auscultation device; and communicating the auscultation sound data file to at least one sound generating device disposed in or on at least one auscultation device.

Still other embodiments relate to an auscultation training device, comprising: an inanimate means for simulating a patient; a means for detecting the relative position of an auscultation device; a means for storing prerecorded auscultation sound data files; a means for selecting one or more prerecorded sound data files from the means for storing; a means for audibly delivering the one or more sound files to at least one ear piece adapted to fit a human ear; and a means for controlling the means for containing, the means for selecting, and the means for delivering.

Further aspects and concepts will become apparent to those skilled in the art after considering the following description and appended claims in conjunction with the accompanying drawings.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION OF THE INVENTION

Some embodiments include a mock auscultation device adapted to present selected sounds to a trainee. In other embodiments, an actual auscultation device is fitted or retrofitted with a means for presenting selected sounds to a trainee. Real and mock auscultation devices can include, without limitation, stethoscopes and are collectively referred to herein as "auscultation devices." Other auscultation devices can also be appropriate depending upon the nature of the intended use. For instance, a mock or actual stethoscope can be appropriate for training medical students to make diagnoses based on body sounds. However, a stethoscope may not be appropriate for training an engineer or technician to recognize diagnostic sounds emanating from a machine. One of ordinary skill in the art will readily recognize the appropriate form that the real or mock auscultation device should take according to the intended use. The following disclosure uses stethoscopes as an exemplary auscultation device; however, the present invention is not limited to such devices.

Some embodiments comprise a system including a medical training mannequin, and at least one auscultation device. Such embodiments include a means for detecting the relative position of an auscultation device in relation to the mannequin and relaying its relative position to a controller device. The controller device is adapted to select sound data from the database that corresponds to the detected location and retrieve, or cause the retrieval of, one or more sounds from the database. According to some embodiments, the controller also communicates the sound data to a transmitter, or causes the sound data to be so communicated. The sound data can then be communicated by the transmitter to at least one receiver that is disposed on or in the at least one auscultation device, such as a stethoscope. The receiver can also be in electronic communication with a sound-generating device adapted to convert electronic signals from the receiver into acoustic wave signals. Such acoustic wave signals can then be audibly communicated to an ear piece and to a human ear.

Some embodiments comprise a system including a medical training mannequin, and at least one auscultation device. Such embodiments include a means for detecting the relative position of an auscultation device in relation to the mannequin and relaying its relative position to a controller device. The controller device is adapted to select sound data from the database that corresponds to the detected location and retrieve, or cause the retrieval of, one or more sounds from the database. According to some embodiments, the controller also communicates the sound data to a transmitter, or causes the sound data to be so communicated. The sound data can then be communicated by the transmitter to at least one receiver that is disposed on or in the at least one auscultation device, such as a stethoscope. The receiver can also be in electronic communication with a sound-generating device adapted to convert electronic signals from the receiver into acoustic wave signals. Such acoustic wave signals can then be audibly communicated to an ear piece and to a human ear.

Some embodiments can include a component, device or system for simulating percussion examinations. For instance, an embodiment can include a device for detecting a percussion impact, and using a signal generated by the detection device to trigger playback of a predetermined sound. Thereby, the embodiment creates the illusion of a percussion exam of a live patient.

In some embodiments a device for detecting auscultatory percussion impacts can comprise one or more of, without limitation, a piezoelectric element, a microphone, a pressure transducer, or a mechanical switch such as a membrane switch. Furthermore, the device can be disposed in one or more advantageous locations. For instance, an impact detection device can be fitted into one or more fingertips of a glove, or affixed to the user's finger. In some embodiments, a mannequin can be fitted with one or more impact sensing devices. For instance, a mannequin can have such a device disposed in an area, such as the chest, where auscultatory percussion is to be conducted. Thus, such embodiments have one or more impact sensitive zones.

Each of the foregoing components can be in communication with one or more of the other components by any appropriate means including wireless and hardwired electronic connections. Furthermore, each component can be physically disposed in an on-board relation to any other component or can be in a remote physical relation to any other component. For example, in some embodiments all of the foregoing components are contained in a single physical unit. In other embodiments each of the foregoing components is remote relative to each of the other foregoing components. Still other embodiments are somewhere between these extremes, wherein some components are grouped together into physical units and others are remote from each other. A wide variety of relations can be appropriate depending on the specific application, and one of skill in the art will be able to select a desired relation without undue experimentation.

Any of a wide variety of wireless communications means can be appropriate for data and/or control signal transmission. For instance, some appropriate means can include radio; IR, IF, or RF signals; or infrared communications means. More specifically, some appropriate protocols include, without limitation WiFi, Bluetooth® (Bluetooth is a registered certification mark of Bluetooth Sig Inc., Bellevue, Wash.), ZigBee® (ZigBee is a registered trademark of ZigBee Alliance Corp., San Ramon, Calif.) and the like. Similarly, any of a wide range of hardwired connections can be appropriate. Some such connections include, without limitation, serial bus, parallel bus, SCSI, I2C (inter-integrated circuit), SPI (serial peripheral interface), and the like or any combination thereof. One of skill in the art will recognize that a wide range of wireless and hardwire technologies are available, and will be able to select an appropriate technology without undue experimentation.

In some embodiments the mannequin is fitted with a means for detecting the relative position of an auscultation device. Such embodiments are capable of determining the region of the mannequin to which a trainee is applying the auscultation device. For example, some embodiments can localize the auscultation device in a heart region, a lung region, any of a variety of visceral or thoracic regions, and the like, or any other region of the body.

According to some embodiments the means for detecting relative position can comprise one or more proximity switches or one or more arrays thereof In such embodiments, the proximity switches, or arrays thereof, are adapted to detect the position of an auscultation device, such as a metallic stethoscope head, relative to the mannequin. The position data can then be communicated to a controller unit.

Alternatively, other embodiments are adapted to triangulate the position of the auscultation device. According to such embodiments, the auscultation device is fitted with a transmitter beacon for broadcasting a predetermined signal. The mannequin includes two or more receivers adapted to receive the transmitter's beacon signal, and data obtained from the receivers can be analyzed according to known algorithms to calculate the position of the auscultation device relative to the mannequin. The present invention is not limited to the use of triangulation or proximity switches. Alternative devices can be used to determine the relative position of an auscultation device, and one of skill in the art will be able to select an appropriate device without undue experimentation.

In some embodiments the controller can be in hardwired electronic communication with the means for detecting the relative position of an auscultation device. For example, in some embodiments the controller can be disposed on or in the mannequin and may be linked to the means for detecting relative position by at least one hardwired electrical connection. In other embodiments, the controller may be hardwired, but also disposed apart from the mannequin, for example, in a desktop or handheld module. In still other embodiments, the controller can be in wireless communication with the means for detecting relative position.

Some embodiments also include a database. Suitable databases can comprise any appropriate data structure such as, without limitation, lists, hash tables, or hierarchical, relational, or network models. In some embodiments the database simply comprises a group of sound files stored together on, for instance, a CD-ROM or flash memory. The database can be stored on any appropriate machine memory means including, without limitations, volatile or nonvolatile memories, EPROMs, EEPROMs, magnetic media such as tapes or hard drives, optical media such as CD-ROMs, and the like or any combination thereof. Furthermore, the database can be physically disposed in any of a variety of locations. For example, in some embodiments the database may be an on-board component of the mannequin. In other embodiments, the database may be a disposed apart from the mannequin and may be a component of the controller unit, or a component of a module hardwired thereto. In still other embodiments the database may be physically disposed in a standalone, desktop or handheld means, or even as a component of the auscultation device.

Sounds can be selected in, and retrieved from, the database by one or more of a variety of means. In some embodiments a sound is automatically selected according to the detected position of the auscultation device. For instance, if the system determines that the auscultation device is positioned over the heart region of the mannequin, then a heart sound is selected.

Alternatively, sound data may be selected and retrieved from the database according to a computer program. For instance, a program may select a particular sound based on several factors including the detected position of the auscultation device, the condition of the simulated patient (e.g. is the simulated patient experiencing a myocardial infarction), and the status of other simulator components (e.g. have chest compressions, defibrillation, or a simulated drug injection been detected). Additionally, some programs may include a weighted randomness factor, wherein the system selects a sound according to several factors, but also includes a degree of randomness in its selection. Still further, some embodiments can comprise selecting a plurality of sounds from one or more databases, and playing them substantially simultaneously.

Still further, in other embodiments one or more sounds may be manually selected by a human operator. For instance, in one example an instructor or other person may observe the placement of the stethoscope over a specific region of the body, and use a remote handheld push-button unit to select an auscultation sound (corresponding with organ functions expected to be audible in the specific location of the stethoscope) for presentation to the trainee.

According to some embodiments one or more sounds can be selected according to any of the foregoing methods, and the selection can comprise a primary sound as well as one or more ancillary, background, or secondary sounds. Therefore, when a listener positions an auscultation device over the heart, for instance, he can experience a heart sound as well as respiratory sounds. According to some embodiments the ancillary, background, or secondary sound(s) can be attenuated or otherwise processed. For instance, a background sound can be attenuated according to its expected prominence relative to a primary sound in a live patient. However, in some embodiments the ancillary, background or secondary sound(s) may not be processed at all.

According to some embodiments, a wide variety of means for combining sounds can be acceptable. In one non-limiting example, a plurality of sound files are stored separately in databases encoded on mutually remote devices such as, without limitation, separate computers, MP3 players or the like. The plurality of sound files are read according to known methods and can then be electronically combined according to one or more schemes. Electronic mixing can include, for instance, combining digital signals or analog signals. In some embodiments, analog signals from two or more media sources can be mixed by splicing electric conductors, e.g. wires, carrying the respective signals together with a common conductor.

In some embodiments, a plurality of electronic audio signals may be separately communicated directly to a sound-generating device such as a speaker. Alternatively, the signals may be communicated as a collection, sum, or superposition of signals, such as through space or on a single physical channel In some embodiments, the plurality of audio signals can be similarly communicated to one or more audio processing devices prior to being communicated to a sound-generating device. Some suitable audio processing devices can, for instance, adjust the amplitude and/or frequency of an audio signal, remove noise, or otherwise alter the audio data signal. Such audio processing devices can include electronic components, software components, or a combination thereof Furthermore an audio processing device may adjust signals carried on separate channels individually or collectively. Still further, in some embodiments, adjustments can be made manually or automatically according to a computer program or predetermined settings.

Accordingly, embodiments can include auscultation sounds being stored on one or a plurality of audio sources, and combined according to any appropriate methods or means so as to produce a more realistic simulated medical examination experience.

Some embodiments also include a transmitter suitable for transmitting auscultation sound data. The transmitter can be physically disposed in any of a variety of locations depending upon the specific application. For instance, the transmitter may be an on-board component of the mannequin, the controller, the database or any combination thereof Accordingly, suitable transmitters can receive auscultation sound data through hardwire connections or wirelessly depending upon the specific architecture adopted. In one embodiment, the controller receives data indicating the position of an auscultation device relative to the mannequin, selects and retrieves one or more corresponding sound files from the database and communicates the sound file(s) through a hardwire connection to the transmitter, which then wirelessly transmits the sound file(s). One of skill in the art will recognize that this is only one of many possible architectures.

Some embodiments also include a receiver adapted to receive signals broadcast by the transmitter. The receiver can be disposed in any appropriate location on or in the auscultation device. For instance, in one embodiment the receiver can be disposed in the head piece of a stethoscope. The receiver can be adapted to convert a signal received from the transmitter into an electrical signal and communicate the signal to a sound generation device such as, without limitation, a speaker. Typically, the receiver is hardwired to the sound generation device; however, this is not required. In one example, the receiver and speaker are disposed in the head piece of a stethoscope. Therefore, the auscultation sound signal is converted into an acoustic wave within the head piece and audibly communicated to a listener's ears in the same way that the stethoscope normally transmits auscultation sounds.

Additionally, some embodiments can include a plurality of auscultation devices each having a receiver. For instance, in one embodiment it may be desirable to have a first auscultation device for a student and a second auscultation device for an instructor, so that the student and instructor can both listen to the same auscultation sound provided by the controller and transmitter. Furthermore, it may be desirable to have an auscultation device for each of a plurality of students and for one or more instructors. Accordingly, an entire class can listen to the same auscultation sound simultaneously through their own devices. This may be especially beneficial, for instance, when an instructor is teaching a class the meaning of a particular sound. In another embodiment, a single transmitter 140 may be capable of providing different sounds, or combinations of sounds, to a plurality of different receivers 150. According to this embodiment, individual students in a classroom could be prompted to identify, for testing or other purposes, a specific irregularity associated with a provided sound or combination of sounds.

Figure 1:
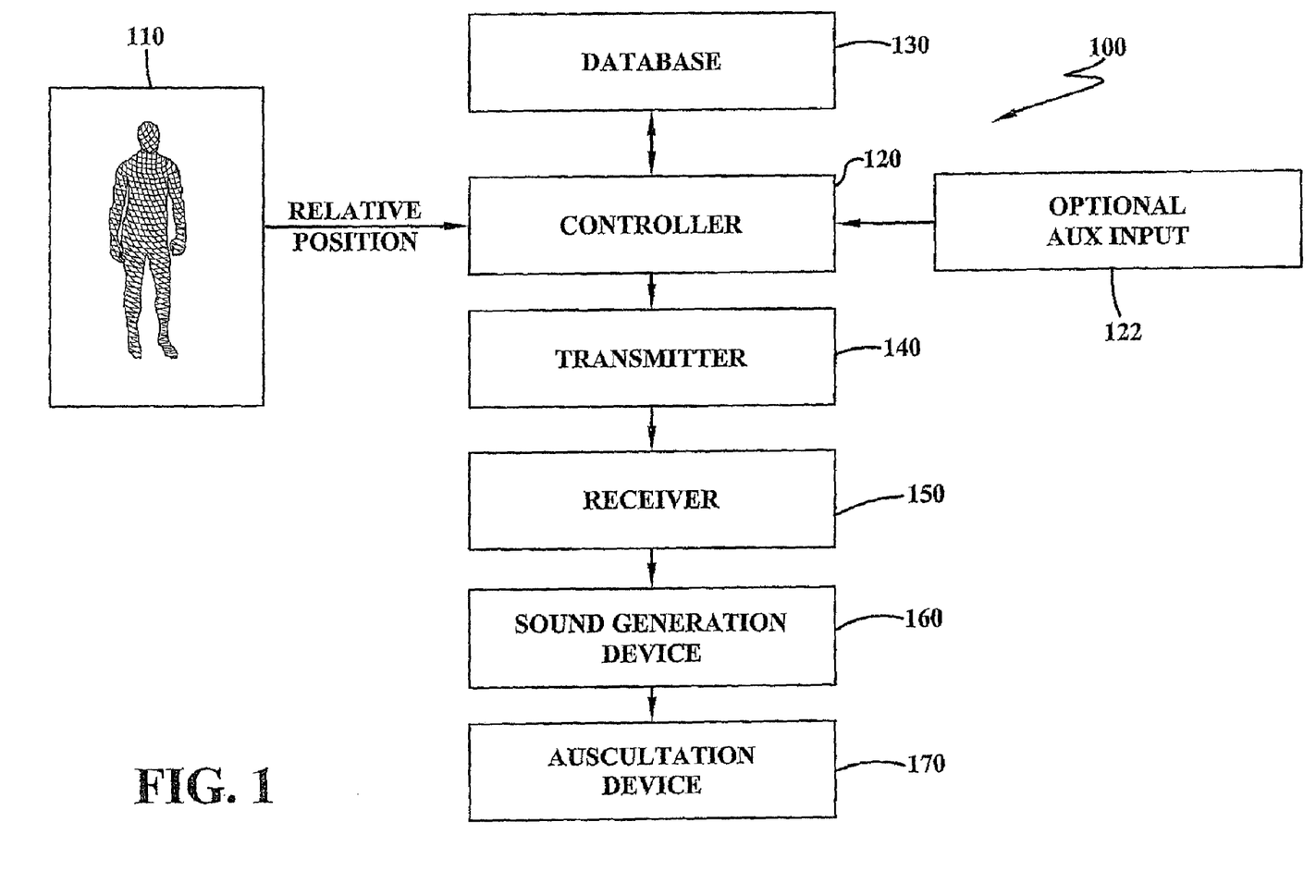
FIG. 1 is a connectivity chart showing the flow of information through an embodiment.

Turning now to the figures, FIG. 1 is a connectivity diagram showing how information generally flows through the embodiment 100. The embodiment 100 includes a mannequin 110 fitted with a means for detecting the relative position of an auscultation device 170. The mannequin 110 communicates position data to controller 120. Controller 120 determines the position of the auscultation device 170 relative to mannequin 110, and thus determines which sound(s), or class of sounds, is appropriate for transmission. For instance, if the auscultation device is found to be proximal to a heart region, then an appropriate sound may be one or more heart sounds and one or more secondary or background sounds such as pulmonary respiration sounds. Accordingly, controller 120 selects an appropriate sound file(s) from database 130 and retrieves the selected sound file(s). The controller 120 then communicates the sound file(s) to a transmitter 140, which wirelessly broadcasts the sound file(s) according to a predetermined protocol. The broadcast signal is received by receiver 150 and communicated to a sound generation device 160, such as a speaker. The sound generation device 160 communicates an acoustic wave through an auscultation device 170, which audibly delivers the acoustic wave to a listener.

Alternatively, controller 120 can receive input manually entered from an instructor or other person into an auxiliary input source 122, such as a pushbutton, a keypad, or other human interface means. Accordingly, some embodiments enable a person, such as an instructor, to select auscultation sounds to be presented to the trainee. Thus, in some embodiments the means for detecting the relative position of the auscultation device can be overridden or even absent entirely.

Figure 2:
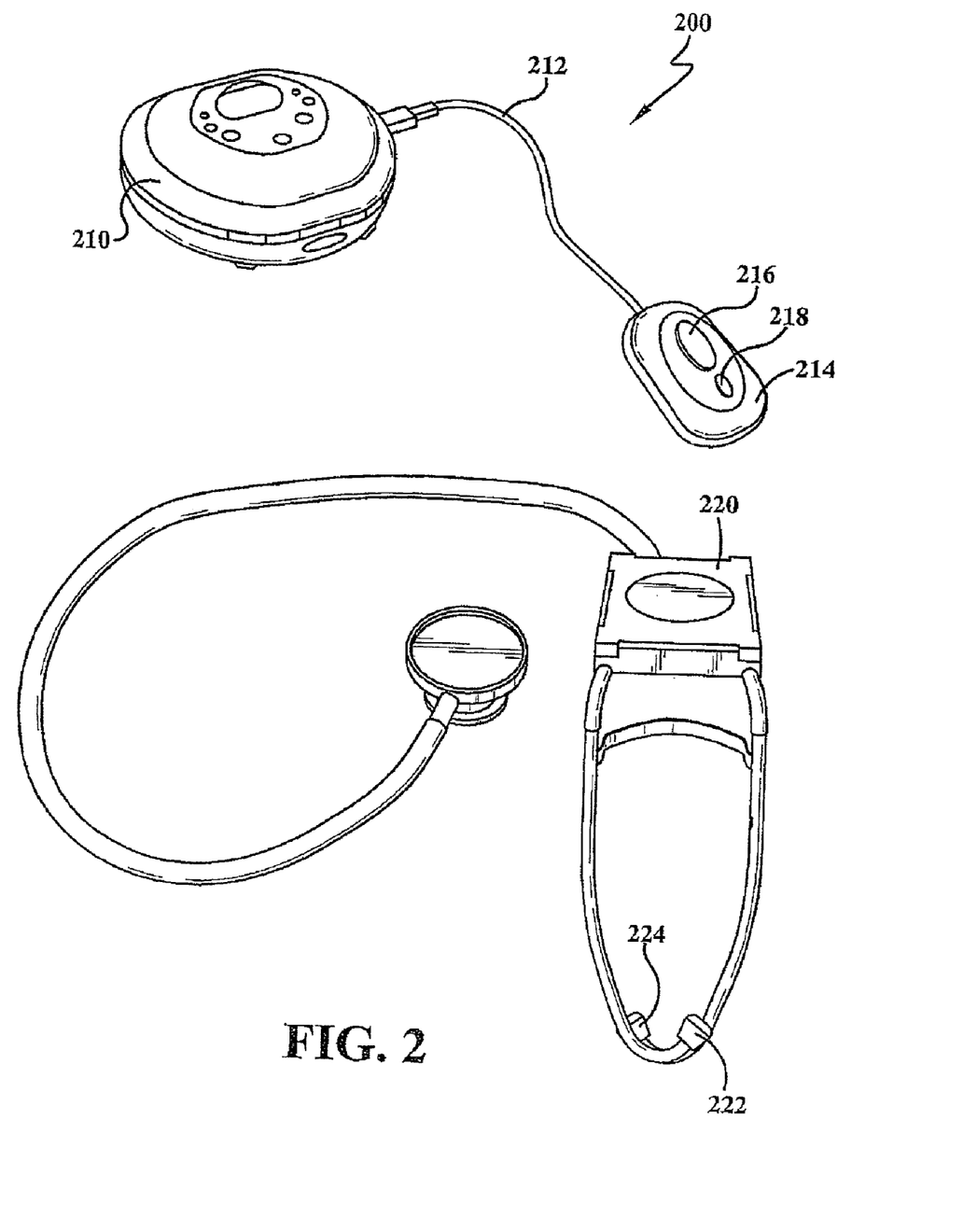
FIG. 2 is a pictorial diagram of an embodiment.

FIG. 2 is a drawing of an embodiment comprising a CD-ROM player 210. The player 210 is hardwired through connection 212 to a handheld controller device 214 comprising a sound selector. According to this example, the CD-ROM player receives push button commands from the controller 214. For example, a user would press button 216 to cursor through a list of sounds and would push button 218 to select the desired sound(s). The selected sound(s) would then be broadcast by CD-ROM player 210 using an appropriate transmitter (not shown). The auscultation device 220 receives the broadcast signal using an appropriate receiver (not shown) and converts the signal into an acoustic wave. The acoustic wave can then be communicated through the auscultation device and audibly delivered to a listener through ear pieces 222, 224.

Figure 3:
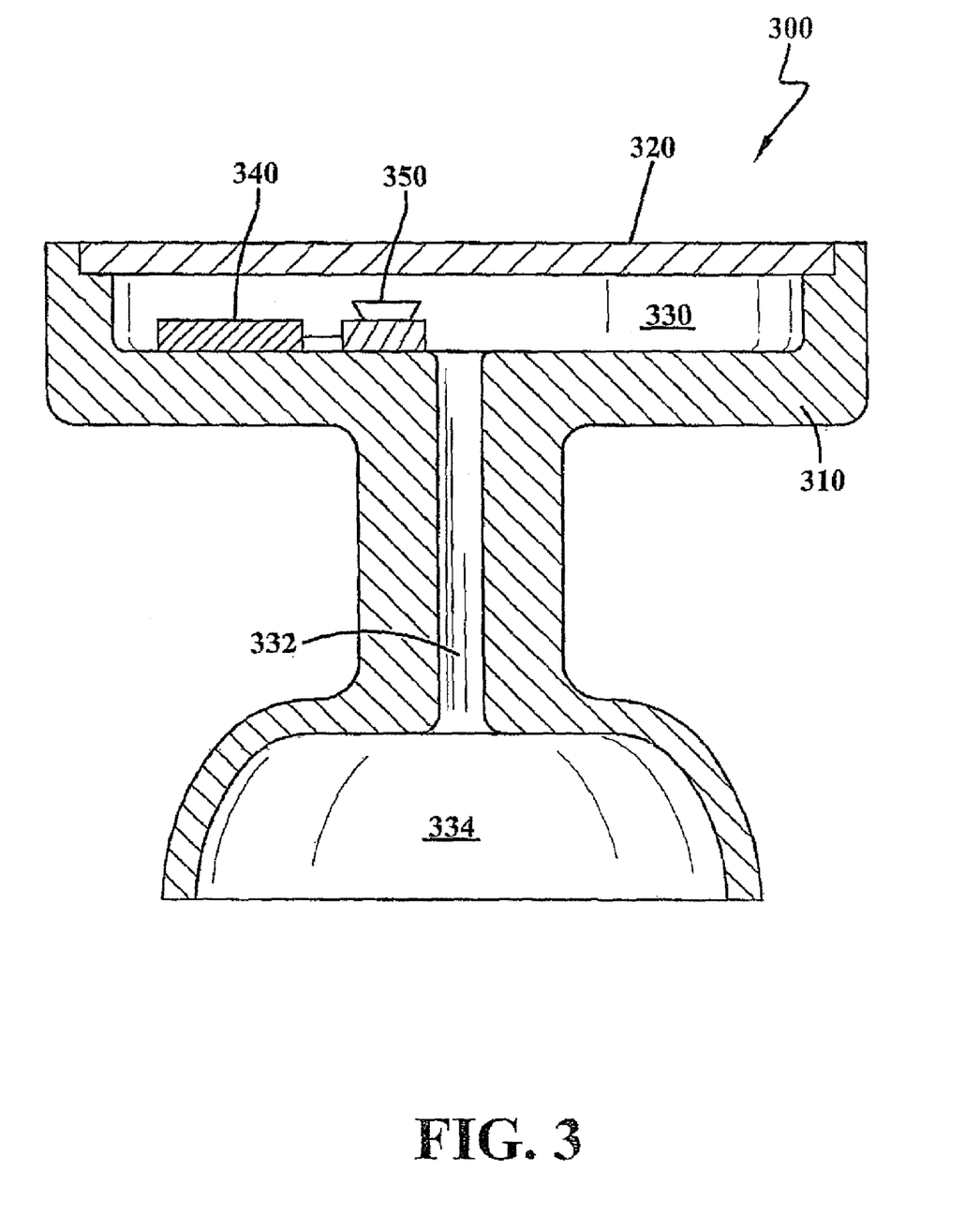
FIG. 3 is a diagram of a head piece of an embodiment.

FIG. 3 is a drawing of an embodiment comprising a head piece of a stethoscope 300. According to the example in FIG. 3, the head piece 300 comprises a body 310 defining a first cavity 330, and a channel 332 in acoustic communication with a second cavity 334. Thus, the first 330 and second 334 cavities are in acoustic communication. The head piece 300 also includes a diaphragm 320. When the auscultation device is used to detect acoustic waves external to the head piece 300, the diaphragm 320 vibrates in resonance with such sounds and generates a duplicate acoustic wave inside the head piece 300, which can be audibly delivered to a listener. However, when the auscultation device is used to listen to sounds transmitted according to the present invention, a sound data signal is received by receiver 340, which is disposed in the first cavity 330 and is mounted on an inner surface of the body 310. The receiver then communicates the received signal to a speaker 350, which generates a corresponding acoustic wave. The acoustic wave is then communicated through the first cavity 330 to the second cavity 334 through the channel 332 and can then be audibly delivered to a listener.

Figure 4:
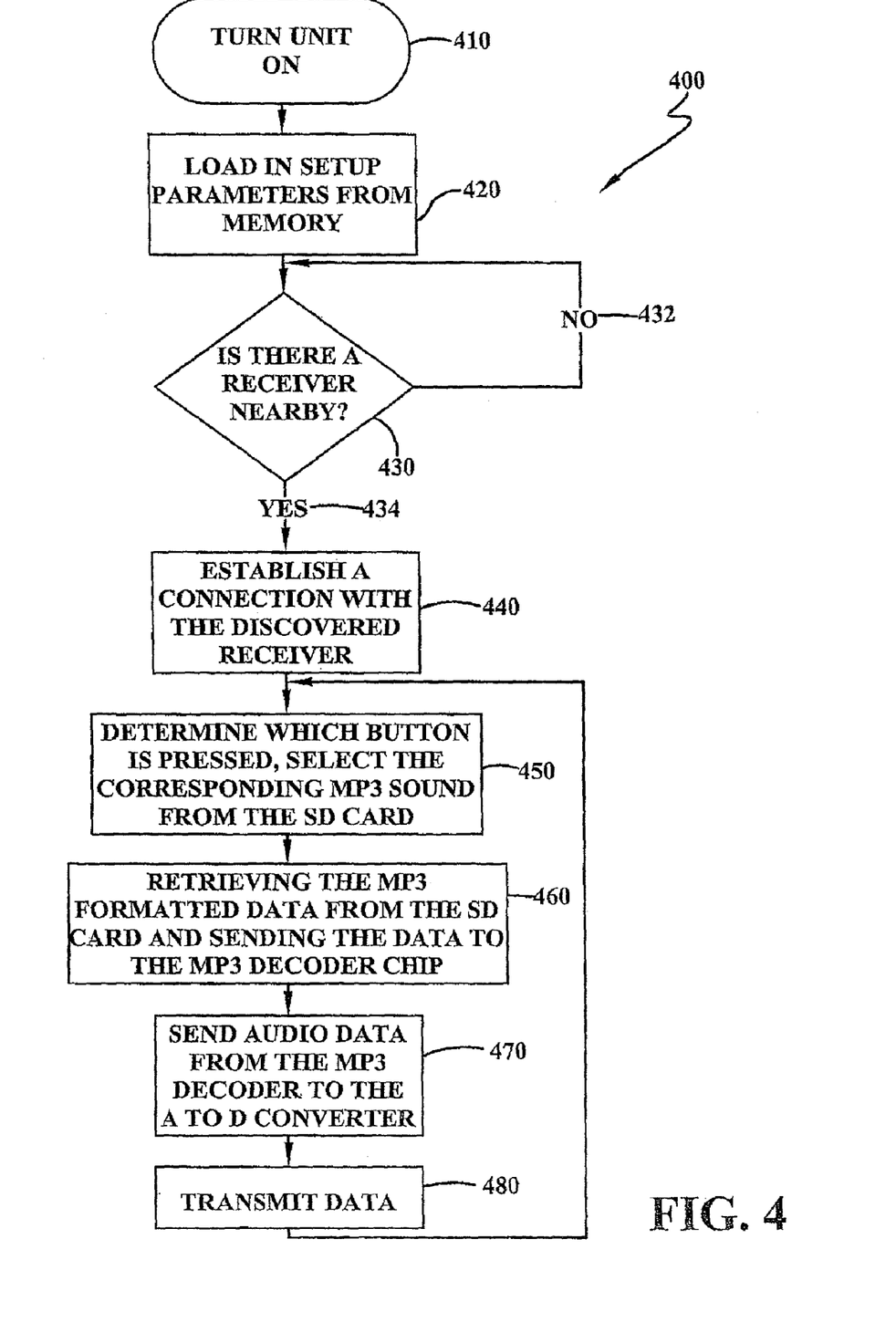
FIG. 4 is a flowchart illustrating the operation of a transmitter embodiment.

FIG. 4 is a flowchart of a process embodiment 400. According to the embodiment 400 a process for operating a transmitter comprises a first step of turning the unit on 410. Another step comprises loading setup parameters in memory 420. The embodiment 400 also includes checking for a receiver within range of the transmitter 430. According to this embodiment, if a receiver is not found the embodiment continues to check 432 for a receiver until one is found or until the process is otherwise terminated such as by disengaging the power, or by issuing a timeout or termination command. When a receiver is found, the process continues 434 to a next step. According to this embodiment the next step comprises establishing a communications connection between the transmitter and receiver 440. According to this process embodiment 400 the device for carrying out the process comprises a plurality of buttons, each button being associated with a predetermined sound file(s). After establishing a connection with the receiver an operator can select and push a button to transmit a corresponding sound(s) to the receiver. In this case the sound file(s) comprises an MP3 format. Accordingly, a next step in the process embodiment 400 comprises detecting that a button has been pushed, determining which button, and selecting the corresponding sound file from a memory device 450. A next step includes retrieving the corresponding sound file and sending the file to an MP3 decoder chip 460. The output of the decoder chip can then be directed to an analog to digital converter 470. The digitized sound file can then be transmitted by the transmitter to the receiver 480. According to this embodiment 400, the steps from 450 to 480 can repeat as needed for each communication session between a transmitter and receiver.

Figure 5:
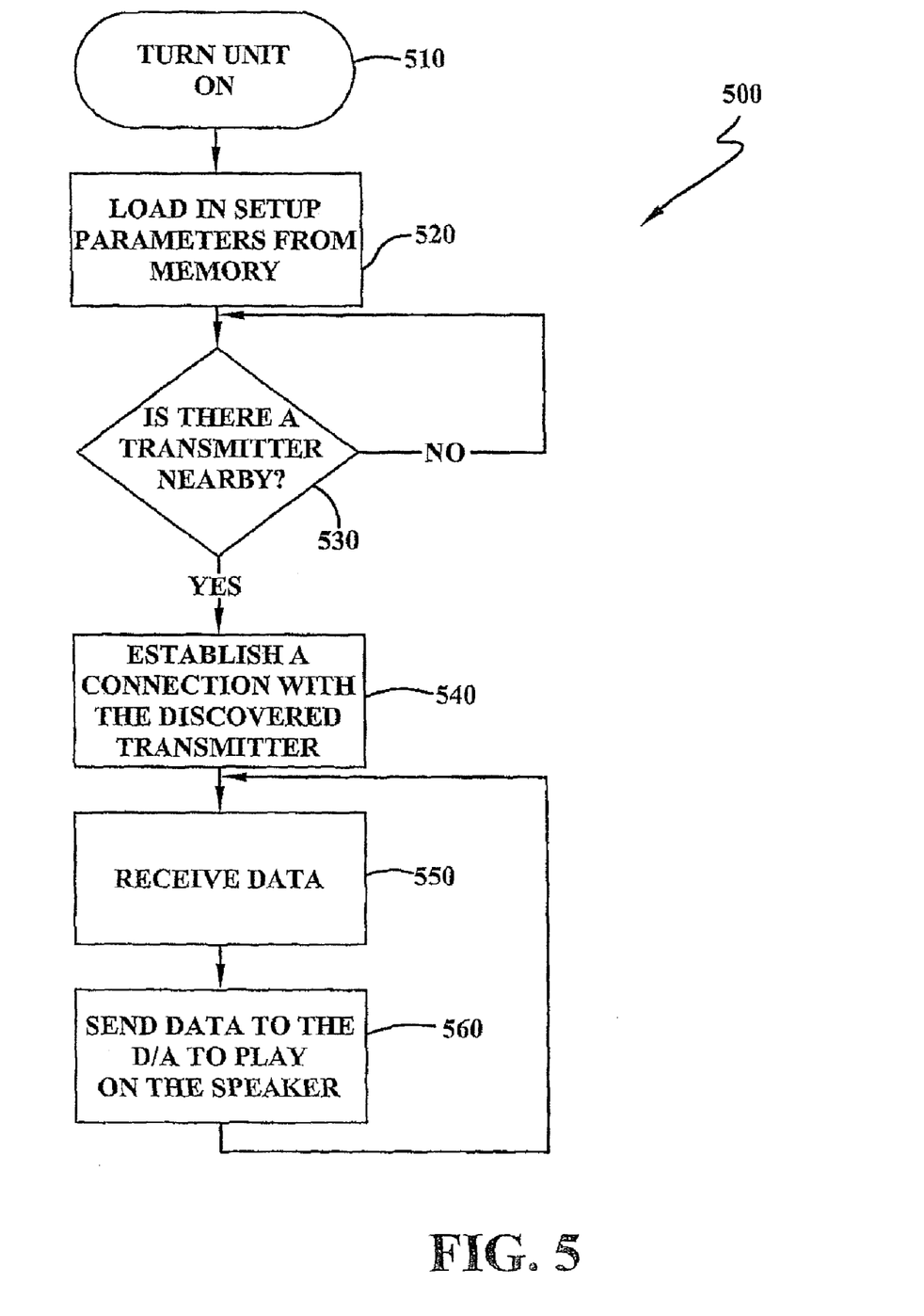
FIG. 5 is a flowchart showing the operation of a receiver embodiment in connection with an audible simulation.

FIG. 5 is a flowchart of a receiver process embodiment 500 of the present invention. According to the embodiment in FIG. 5 a first step in a process for operating a receiver of the present invention includes turning on 510 the receiver unit. A second step includes loading 520 setup parameters in memory. A next step includes determining 530 whether there is a transmitter within range of the receiver. According to the embodiment 500 shown in FIG. 5 if no transmitter is detected, the receiver continues attempting to find a transmitter until one is found, or until the process is otherwise terminated such as by turning off power to the unit, or issuing a timeout or termination command Assuming a transmitter is found in step 540, the next step is establishing 540 a communications connection between the transmitter and receiver. After establishing a connection, a next step according to embodiment 500 is receiving 550 data from the transmitter. According to process embodiment 500 data received from the transmitter can be routed 560 to a digital-to-analog converter. The output of the converter can be directed to a speaker to produce an audible sound corresponding to the MP3 file from which it originated.

Figure 6:
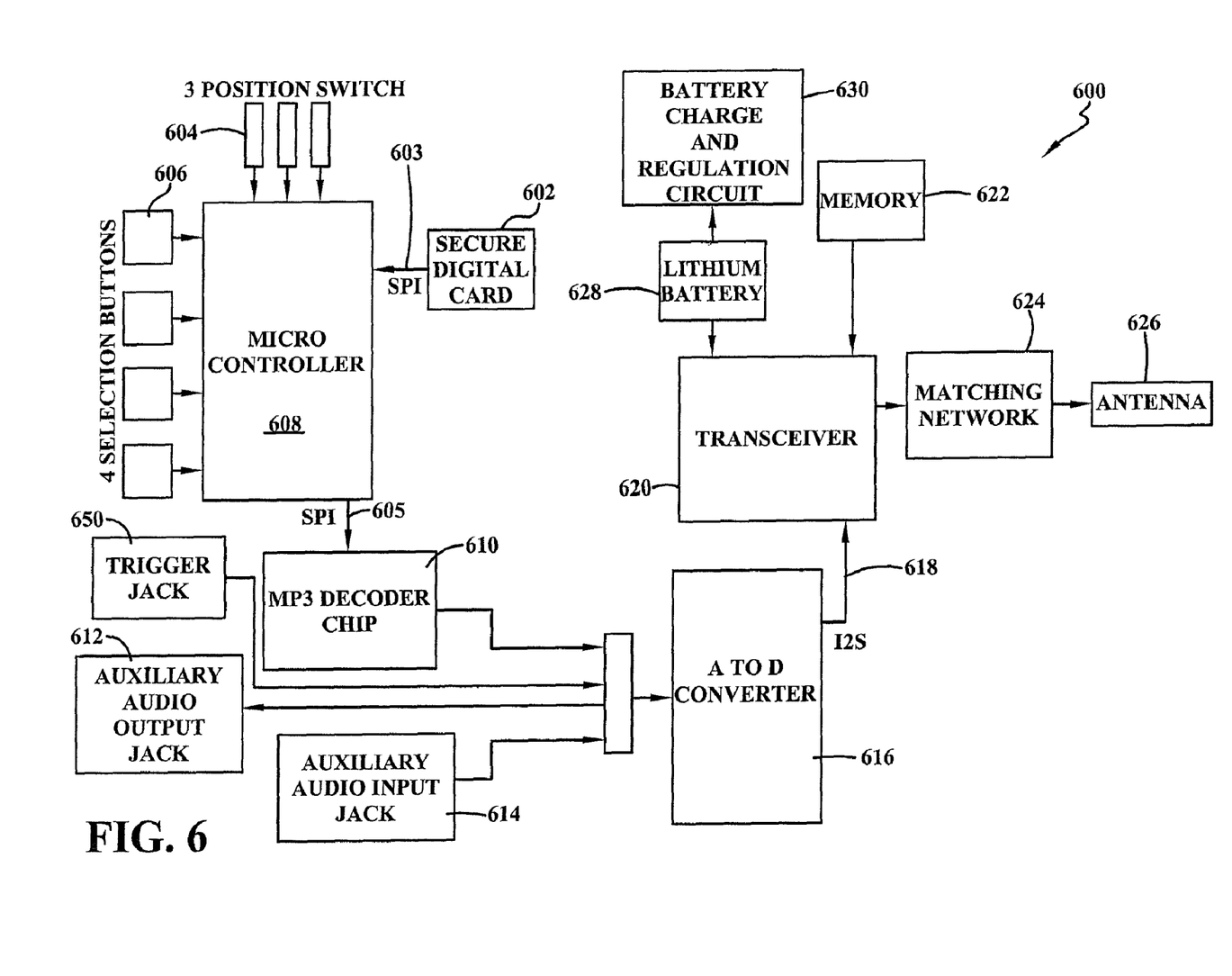
FIG. 6 is a schematic diagram of a transmitter circuit embodiment.

FIG. 6 is a block diagram of a transmitter embodiment 600. According to this embodiment a Secure Digital card 602, i.e. SD card, is adapted to contain electronic data comprising one or more audio files, such as an MP3 file(s). The card can be removably inserted into an onboard SD card reader. The SD card reader is in electronic communication with a microcontroller 608 through a SPI serial bus 603. The microcontroller 608 is also in electronic communication with a three position switch 604, which is adapted to select a set of one or more sounds. Additionally, the microcontroller 608 is also in electronic communication with a set of four selection buttons 606, which are adapted to select audio files contained on the SD card 602. Thus, when an operator pushes one of the set of four buttons it causes a predetermined audio file to be read and directed to MP3 decoder chip 610 through SPI serial bus 605. The analog output of the MP3 decoder chip 610 can be directed to analog-to-digital converter 616, which accepts it as input and directs the resulting digital output to transceiver 620 through I2S serial bus 618.

Transceiver 620 is also in bidirectional electronic communication with memory 622. Accordingly, transceiver 620 is adapted to transfer data to and from memory 622. Additionally, according to FIG. 6, transceiver 620 in electrical communication with a lithium battery 628, which provides transceiver 620 with a power source. Furthermore, lithium battery 628 electrically interfaces with transceiver 620 through battery charge and regulation circuit 630 which is adapted to extract electrical power from battery 628 and provide it to transceiver 620 according to predetermined criteria. According to some embodiments regulation circuit 630 is also adapted to regulate battery recharging processes. Finally, transceiver 620 is in electronic communication with a matching network 624, which is adapted to match the transceiver's 620 output impedance with the input impedance of a receiver. Matching network 624 then communicates the electronic signal to broadcasting antenna 626, which is adapted to broadcast the MP3 audio file.

According to FIG. 6 embodiment 600 also includes auxiliary audio output jack 612, which is adapted to receive signals from MP3 decoder chip 610 and direct such signals, or a portion thereof, to an external circuit. Further according to FIG. 6, embodiment 600 includes auxiliary audio input jack 614. Therefore, embodiment 600 is adapted to receive audio data from sources other than an SD card, and in formats other than MP3. In some embodiments, plugging an audio source into audio input jack 614 causes the MP3 player to be disconnected, and only the audio streaming from jack 614 is transmitted. In still other embodiments, the embodiment 600 additionally includes a trigger jack 650; plugging an external component—having an activated external triggering mechanism—into trigger jack 650 can cause a prerecorded sound to be transmitted to the receiver 150.

Figure 9:
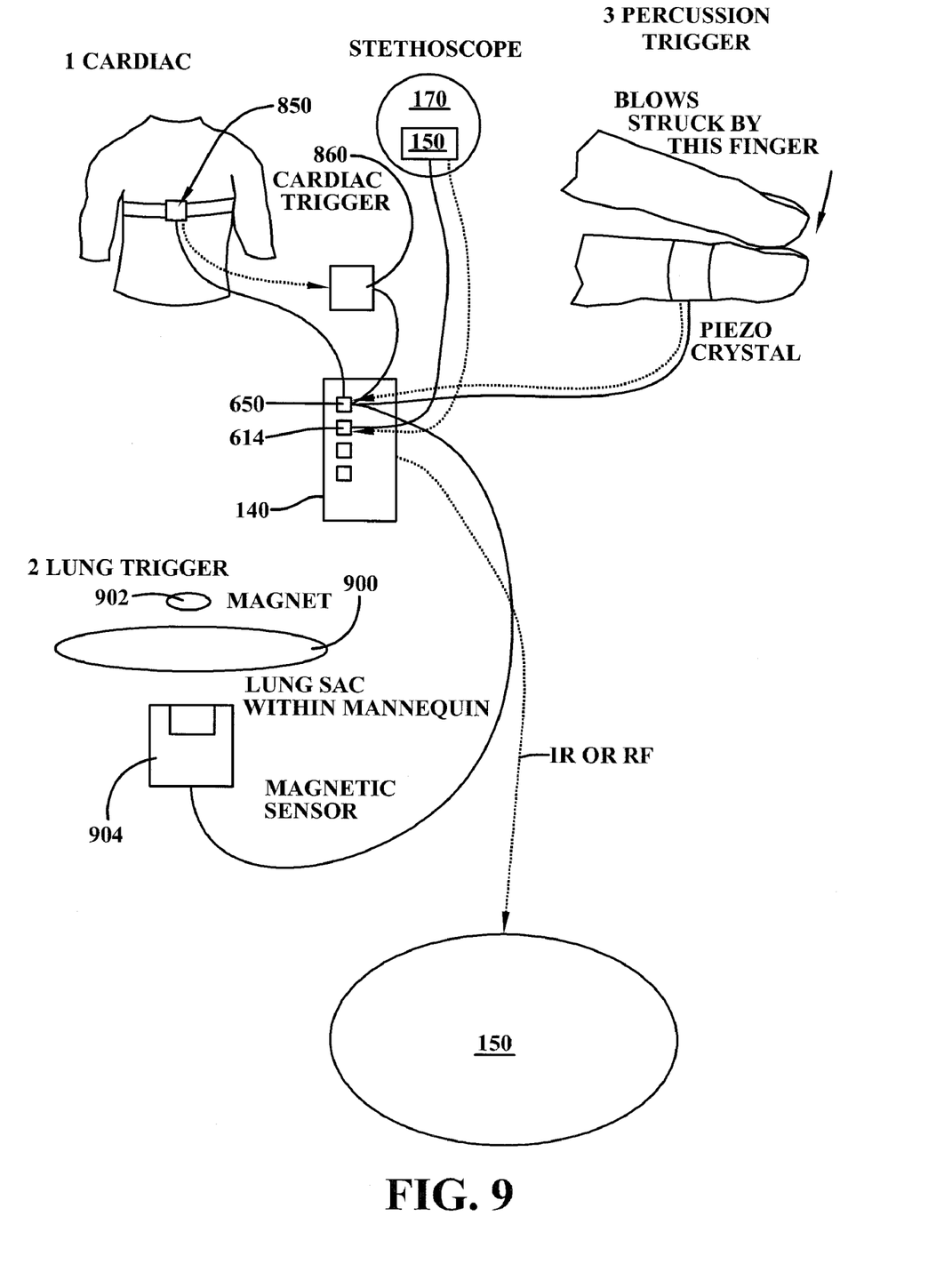
FIG. 9 is a schematic representation of a representative sampling of components that can be received within the auxiliary audio input jack.

In some embodiments, as generally illustrated in FIGS. 6 and 9, the input jack 614 is adapted to disable the use of prerecorded sounds and instead receive audio sounds from an external source. By way of one non-limiting example, the input jack 614 could receive an output jack from a microphone 800 hardwired into a stethoscope, or a plug-in receiver that receives an output signal transmitted wirelessly from an external auscultory examination device, in a manner that permits a physician or other person to remotely monitor a patient's condition. Such embodiment would be useful for the remote examination of a patient placed in isolation as a result of exposure to harmful biological, chemical, or radiation, without exposing the physician to such harmful contaminants. Such embodiment would also be useful in telemedicine situations where a physician cannot be physically present to examine a patient.

In other embodiments, generally illustrated in FIGS. 6 and 9, the trigger jack 650 is adapted to receive signals generated in response to an external triggering mechanism; with one non-limiting example being signals provided by a system for simulating percussion examinations. In one embodiment, generally described above, a detection device (such as a properly positioned piezoelectric crystal) senses a percussion impact, and generates an electronic pulse signal that is transmitted into the trigger jack 650 to initiate playback of a predetermined sound.

In still other embodiments, the trigger mechanism might comprise any device known by a person of ordinary skill in the art to monitor the heart; such as, by way of non-limiting example, a heart rate monitor band 850 positioned about the patient's or a mannequin's chest region. In this embodiment, the heart rate monitor band 850 senses a change in the electrical field across the patient's or mannequin's chest (in a manner similar that employed by an electrocardiogram, or EKG), and sends a signal to the transmitter, either through a hardwire directly received by the trigger jack 650, or wirelessly to a cardiac trigger box 860 that is received within the trigger jack 650. Receipt of said signal in the trigger jack 650 initiates playback of a prerecorded sound, that can optionally be synchronized with the EKG tracing of a human or mannequin, to provide the user with information regarding the timing of the sound in the cardiac cycle.

In still other embodiments, the triggering mechanism might comprise any device, known by a person of ordinary skill in the art, to monitor or simulate lung functioning. In one possible embodiment, generally illustrated in FIG. 9, an expandable nylon lung sack 900 is positioned within a mannequin; the lung sack has a magnet 902 positioned opposite a sensor (such as, by way of non-limiting example, a sensor tetic flux); when the lung sack 900 is inflated, it moves the magnet 902 away from the sensor, resulting in a change in the magnetic field and/or magnetic flux that is recognized by a sensor 904; the sensor 904 then sends a signal which is received by the trigger jack 650 and activates the playback of a prerecorded sound, which is then transmitted to the receiver 150.

Figure 7:
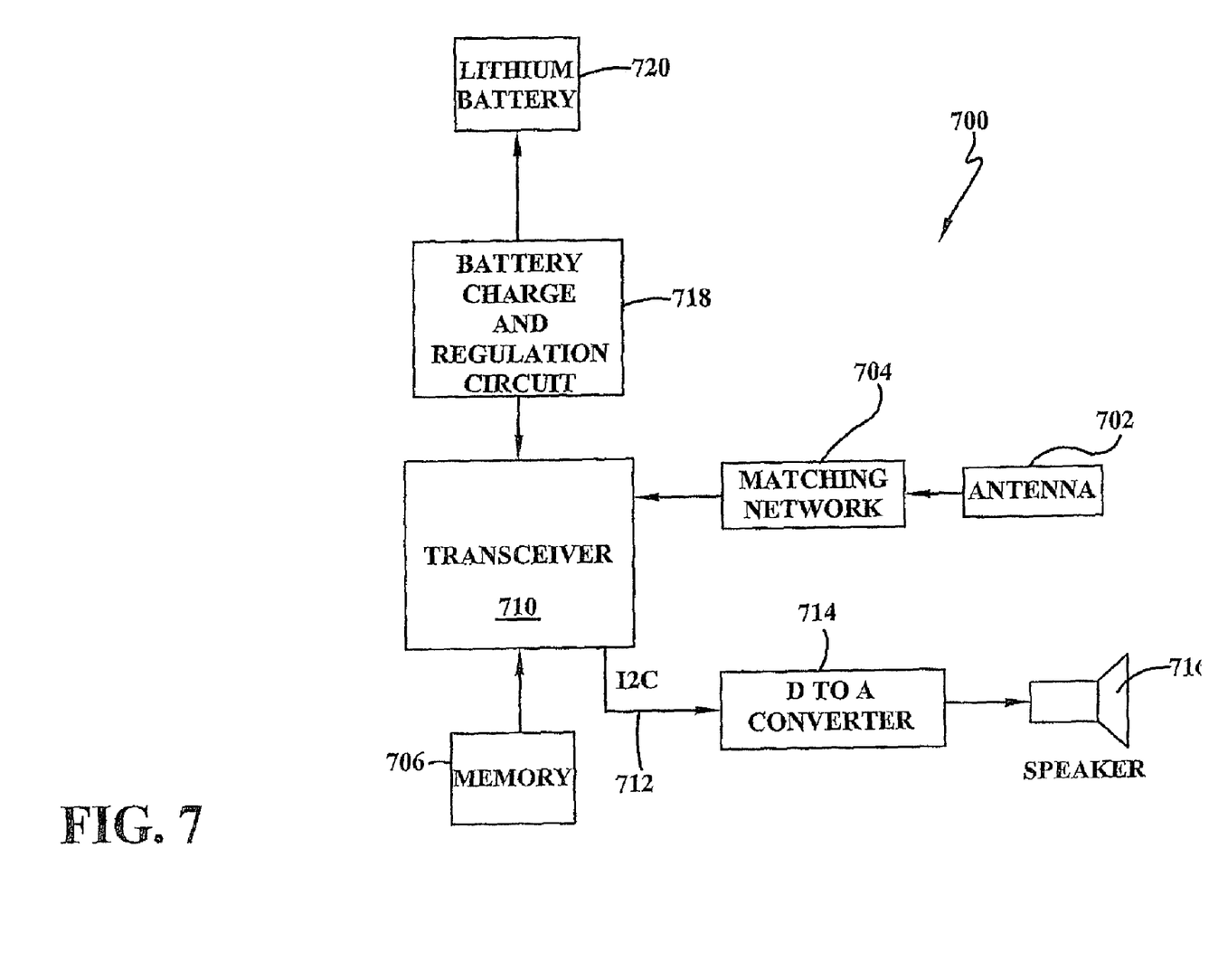
FIG. 7 is a schematic diagram of a receiver circuit embodiment.

FIG. 7 is a block diagram of a receiver embodiment 700. Receiver 700 includes a receiving antenna 702, which is in electronic communication with matching network 704. Matching network 704 is adapted to match the impedance of receiver 700 to the impedance of transmitter 600. Matching network 704 is also in electronic communication with transceiver 710 and is adapted to communicate received signals to transceiver 710. The output of transceiver 710 can be communicated to speaker 716 through digital-to-analog converter 714. Transceiver 710 is also in bidirectional communication with memory 706. Accordingly, transceiver 710 can upload data to memory 706 and/or download data from memory 706 and direct the data to speaker 716. In some embodiments memory 706 is adapted to function as a buffer memory. Transceiver 710 is in electrical communication with lithium battery 720, which provides transceiver 710 with electrical power for operation. Lithium battery 720 communicates electrical power to transceiver 710 through battery charge and regulation circuit 718. Battery charge and regulation circuit 718 is adapted to extract electrical power from battery 720 and provide it to transceiver 710 according to predetermined criteria. According to some embodiments battery charge and regulation circuit 718 is also adapted to regulate battery recharging processes.

Turning to FIG. 8, several audio mixing schemes are illustrated. According to FIG. 8A, an embodiment includes three separate audio sources A1, A2, and A3, which can include storage media and/or playback devices; of course, it is to be understood that a person of ordinary skill in the art would recognize that the invention could include as many more audio sources as necessary. According to this embodiment, the audio sources A1, A2, and A3 each comprise an electronic analog audio signal output. Furthermore, the audio sources A1, A2, and A3 are in communication with a signal processing means 804, such as a hardware and/or software component for manipulating one or more audio characteristics. According to FIG. 8A, the audio signals from the respective sources are communicated along lines 802a, 802b, and 802c. Lines 802a, 802b, and 802c can comprise wires for conducting electrical signals, or can be free space through which an electromagnetic signal is transmitted. As shown in FIG. 8A the processor 804 combines the plurality of input signals into a single output signal communicated along line 806 to a sound-generating device 808, which converts the electronic signal to an audible acoustic signal. Of course, it should be understood that sounds may be combined by any means known to a person of skill in the art; including, for example, the use of physical tubes.

Figure 8A:
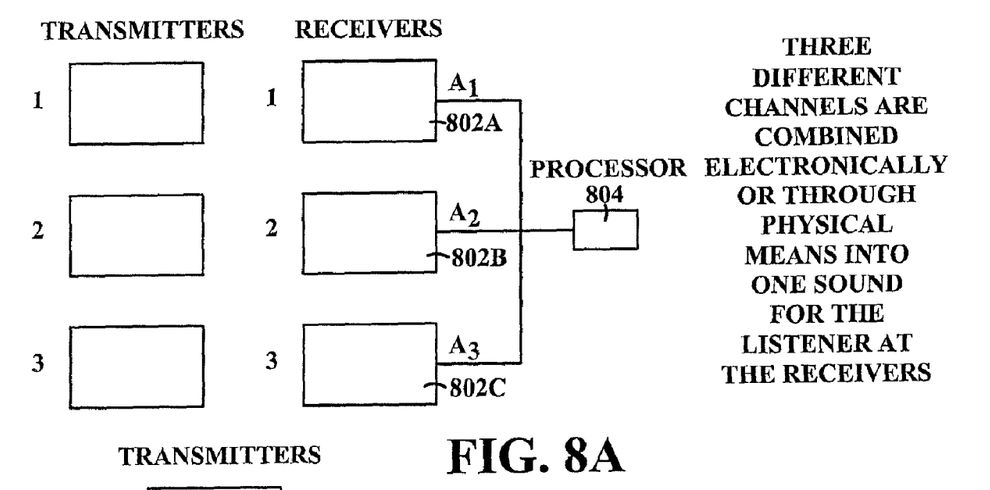
FIG. 8 is a schematic diagram generally depicting means of mixing audio signals according to some embodiments.
Figure 8B:
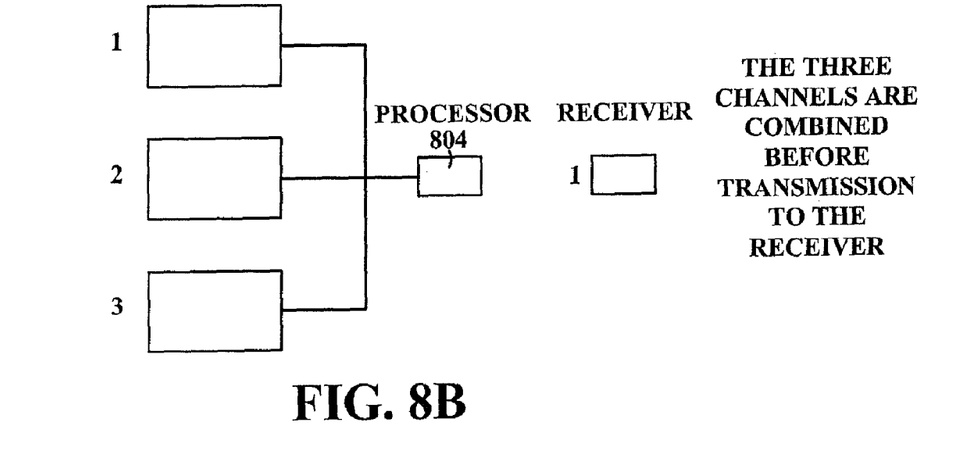
Figure 8C:
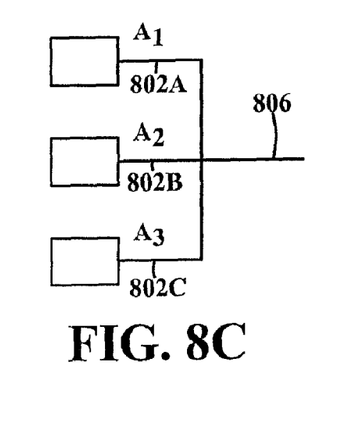
Figure 8D:
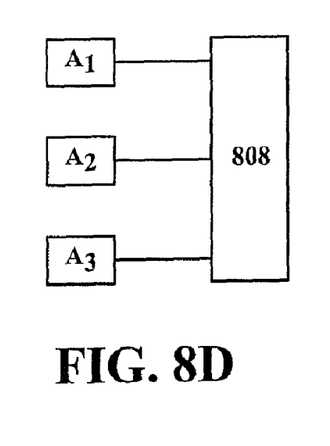

FIG. 8B is similar to 8A, but in this instance the processor 804 does not combine the inputs into a single output, but rather maintains them as separate channels and/or through-space signals 806a, 806b, and 806c. FIG. 8C, is similar to 8A, but lacks a processor. In this instance, the channels 802a, 802b, and 802c are combined by splicing them 803 with a common channel 806. Accordingly, this embodiment can be practiced using physical structures such as wires. FIG. 8D shows the plurality of audio sources A1, A2, and A3 in direct communication with a sound-generating device 808, through lines 802a, 802b and 802c. Similar to the embodiments shown in FIGS. 8A and 8B, lines 802a, 802b and 802c can comprise physical structures such as wires or can comprise free space through which an electromagnetic signal is transmitted.

The embodiments have been described, hereinabove. It will be apparent to those skilled in the art that the above methods and apparatuses may incorporate changes and modifications without departing from the general scope of this invention. It is intended to include all such modifications and alterations insofar as they come within the scope of the appended claims or the equivalents thereof.

I claim:

1. An auscultation training device, comprising:
   a medical training mannequin including a means for detecting relative position of an auscultation device relative to the mannequin;
   a controller in electronic communication with the means for detecting relative position, the controller adapted to receive location data from the means for detecting relative position, wherein the location data indicates the position of the auscultation training device relative to the medical training mannequin, the controller adapted to select and retrieve auscultation sound data from a database in electronic communication with the controller, wherein the auscultation sound data corresponds to the location data received from the means for detecting relative position;
   a sound generating device in electronic communication with the database and adapted to convert the auscultation sound data into acoustic wave signals;
   an auscultation device having at least one ear piece in acoustic communication with the sound generating device and adapted to transmit acoustic wave signals to a human ear; and
   a trigger mechanism in electronic communication with the controller, the trigger mechanism providing a signal to the controller to initiate the playback of a prerecorded sound when the trigger mechanism is activated, wherein the trigger mechanism comprises a detection device which is activated when the detection device senses a percussion impact.

2. The device of claim 1 wherein the sound generating device receives and converts the plurality of auscultation sound data files into acoustic wave signals substantially simultaneously.

3. The device of claim 1 wherein the plurality of auscultation sound data files are electronically combined before the sound generating device receives and converts the combined sound file into acoustic wave signals.

4. The device of claim 1 wherein the controller is further adapted to select and retrieve a primary auscultation sound data file and a secondary auscultation sound data file from the database and cause transmission of the data files representing the plurality of auscultation sounds to the sound generation device for substantially simultaneous playback.

5. The device of claim 4, wherein the secondary auscultation sound data is adjusted to a predetermined intensity relative to the primary auscultation sound data.

6. The device of claim 1 wherein the database comprises a plurality of databases, wherein each database includes a plurality of auscultation sound data files.

7. The device of claim 1 wherein the database is read using a device selected from one or more of an MP3 player, a compact disk player, a computer, or a flash drive.

8. The device of claim 1 further comprising:
   a transmitter in electronic data communication with the database and adapted to receive one or more auscultation sound data signals and transmit the signal; and
   at least one receiver disposed in or on at least one auscultation training device, the receiver being adapted to receive auscultation sound data signals from the transmitter.

9. The device of claim 8, wherein the controller, the database, the transmitter, the receiver, and the sound generating device are each independently adapted to be in electronic communication with at least one other component, and each independently through one or more of an on-board hardwire electronic connection, a remote hardwire electronic connection, or a remote wireless connection.

10. The device of claim 8, wherein the at least one receiver comprises a plurality of receivers each disposed in a different auscultation device.

11. An auscultation training device, comprising:
   a medical training mannequin including a means for detecting relative position of an auscultation device relative to the mannequin;
   a controller in electronic communication with the means for detecting relative position, the controller adapted to receive location data from the means for detecting relative position, wherein the location data indicates the position of the auscultation training device relative to the medical training mannequin, the controller adapted to select and retrieve auscultation sound data from a database in electronic communication with the controller, wherein the auscultation sound data corresponds to the location data received from the means for detecting relative position;

a sound generating device in electronic communication with the database and adapted to convert the auscultation sound data into acoustic wave signals;

an auscultation device having at least one ear piece in acoustic communication with the sound generating device and adapted to transmit acoustic wave signals to a human ear; and a trigger mechanism in electronic communication with the controller, the trigger mechanism providing a signal to the controller to initiate the playback of a prerecorded sound when the trigger mechanism is activated, wherein the trigger mechanism comprises:

a lung sack positioned within the chest of the medical training mannequin; and a detection device which is activated when a lung sack inflates.

12. The device of claim 11 wherein the sound generating device receives and converts the plurality of auscultation sound data files into acoustic wave signals substantially simultaneously.

13. The device of claim 11 wherein the plurality of auscultation sound data files are electronically combined before the sound generating device receives and converts the combined sound file into acoustic wave signals.

14. The device of claim 11 wherein the controller is further adapted to select and retrieve a primary auscultation sound data file and a secondary auscultation sound data file from the database and cause transmission of the data files representing the plurality of auscultation sounds to the sound generation device for substantially simultaneous playback.

15. The device of claim 14 wherein the secondary auscultation sound data is adjusted to a predetermined intensity relative to the primary auscultation sound data.

16. The device of claim 11 wherein the database comprises a plurality of databases, wherein each database includes a plurality of auscultation sound data files.

17. The device of claim 11 wherein the database is read using a device selected from one or more of an MP3 player, a compact disk player, a computer, or a flash drive.

18. The device of claim 11 further comprising:

a transmitter in electronic data communication with the database and adapted to receive one or more auscultation sound data signals and transmit the signal; and at least one receiver disposed in or on at least one auscultation training device, the receiver being adapted to receive auscultation sound data signals from the transmitter.

19. The device of claim 18 wherein the controller, the database, the transmitter, the receiver, and the sound generating device are each independently adapted to be in electronic communication with at least one other component, and each independently through one or more of an on-board hardwire electronic connection, a remote hardwire electronic connection, or a remote wireless connection.

20. The device of claim 18, wherein the at least one receiver comprises a plurality of receivers each disposed in a different auscultation device.

* * * * *